United States Patent [19]

Gilbertson et al.

[11] 4,340,628

[45] Jul. 20, 1982

[54] ANTIBACTERIAL AGENT AND METHOD

[76] Inventors: John R. Gilbertson, 354 Jefferson Dr., Pittsburgh, Pa. 15228; Richard J. Crout, 2122 Pendleton Dr., Monroeville, Pa. 15146

[21] Appl. No.: 97,405

[22] Filed: Nov. 26, 1979

Related U.S. Application Data

[62] Division of Ser. No. 6,347, Jan. 25, 1979, Pat. No. 4,209,533.

[51] Int. Cl.³ .................... A61K 7/16; A61K 31/045
[52] U.S. Cl. ........................... 424/49; 424/343; 426/330.4; 426/532
[58] Field of Search .............. 424/343, 49; 426/330.4, 426/532

[56] References Cited

U.S. PATENT DOCUMENTS

| | | | |
|---|---|---|---|
| 1,914,100 | 6/1933 | Bennett | 424/346 X |
| 3,052,607 | 9/1962 | Hirsh | 424/343 X |
| 3,226,295 | 12/1965 | Goetz et al. | 424/343 |
| 3,383,284 | 5/1968 | Bell et al. | 424/343 |
| 3,458,625 | 7/1969 | Ensor et al. | 424/343 X |
| 3,584,115 | 6/1971 | Gebhart et al. | 424/343 X |
| 3,703,578 | 11/1972 | Cella et al. | 424/49 |
| 3,830,832 | 8/1974 | Suzuki | 424/343 X |
| 3,919,408 | 11/1975 | Mitchell et al. | 424/49 |
| 3,970,759 | 7/1976 | Frankenfeld et al. | 424/343 |
| 4,209,533 | 6/1980 | Gilbertson et al. | 424/343 |

FOREIGN PATENT DOCUMENTS

| | | |
|---|---|---|
| 1492912 | 8/1970 | Fed. Rep. of Germany . |
| 2440436 | 3/1975 | Fed. Rep. of Germany . |

OTHER PUBLICATIONS

Sands et al., Antimicrob. Agents Chemother. 15(1):67–73 (1979), CA. 90, #133352w (1979).
AAES–Jorgenson et al., Biochem. Lipides Proc. Int. Conf., 5th Vienna (1958):134–142 (1960), C.A. 55#7570F (1961).
AAES–Jorgenson et al., J. Nutrition 67:413–442 (1959), C.A. 53#20331g (1959).
Turpenen, J. Nutrition 15:351–366 (1938), C.A. 32 #7526g (1938).
Kabara Antimicrob. Agents Chemother. 2:23–28 (1972).

*Primary Examiner*—Shep K. Rose

[57] ABSTRACT

A method of inhibiting growth of bacteria comprising exposing the bacteria to an effective concentration of a polyunsaturated long-chain alcohol selected from the group consisting of linolenyl alcohol and linoleyl alcohol. The bacteria may be selected from the group consisting of *Clostridium butyricum, Clostridium perfringens, Streptococcus mutans, Streptococcus mutans BHT* and *Streptococcus sanguis.*

A bactericidal product comprising an orally administerable product. The orally administerable product contains an effective concentration of antibacterial compound selected from the group consisting of linolenyl alcohol and linoleyl alcohol to produce an orally administerable product which will resist growth of bacteria selected from the group consisting of *Clostridium butyricum, Clostridium perfringens, Streptococcus mutans, Streptococcus mutans BHT* and *Streptococcus sanguis.*

4 Claims, 4 Drawing Figures

ANTIBACTERIAL AGENT AND METHOD

CROSS REFERENCE TO RELATED APPLICATION

This application is a division of U.S. Ser. No. 6,347, filed Jan. 25, 1979, now U.S. Pat. No. 4,209,533.

BACKGROUND OF THE INVENTION

1. Field of the Invention

This invention relates to bactericidal products and the method of using the same and, more specifically, it relates to the advantageous use of certain polyunsaturated long-chain alcohols to resist growth of certain bacteria.

2. Description of the Prior Art

The desirable bactericidal effect of numerous compositions employed in pharmaceuticals, soaps and in other instances where it is advantageous to destroy certain bacteria have long been known.

It has previously been suggested that fatty acids and derivatives may advantageously be employed effectively against certain bacteria. See Kabara, Swieczkowski Conley and Traunt, Antimicrobial Agents and Chemotherapy, Vol. 2, pages 23–28 (1972). Of the nine straight-chain fatty acids tested by Kabara et al on selected bacteria lauric acid was found to be the most effective bacteriostatic agent with selected gram-positive organisms. This article also notes lauryl alcohol is more effective than the corresponding acid.

The antifungal and bactericidal properties of fatty acids have been well known. In general, fatty acids function as effective anionic surface agents. One of the main reasons for their limited use, however, is reduced potency at human physiological pH values.

There remains a need for an effective antibacterial agent which may be employed in such uses as an additive in foods to reduce the likelihood of bacterial contamination creating a risk of food poisoning and use in orally administerable products other than food such as toothpaste and mouthwash to resist the likelihood of bacteria induced dental cavities and periodontal problems. The need for such an antibacterial agent which can be used in products such as face creams, skin salves, cosmetics and other products to treat or prevent skin infections caused by bacteria such as acne, for example, also exists.

SUMMARY OF THE INVENTION

The present invention has produced a solution to the above described need by providing a method and product for effectively resisting undesired bacterial growth. More specifically, a polyunsaturated long-chain alcohol selected from the group consisting of linolenyl alcohol and linoleyl alcohol has been found to effectively inhibit growth of bacteria selected from the group consisting of *Clostridium butyricum, Clostridium perfringens, Streptococcus mutans, Streptococcus mutans BHT* and *Streptococcus sanguis.* It has been found that these bactericidal compounds may be provided in orally consumable and locally applied products in order to resist undesired bacterial growth.

It is an object of the present invention to provide an antibacterial agent which effectively resists growth of certain undesired bacteria.

It is yet another object of this invention to provide for inclusion of these antibacterial agents in food products, mouthwash, toothpaste and other orally administerable items as well as locally applied products such as face creams, skin salves and cosmetics.

It is a further object of the present invention to provide for such antibacterial agents as a food additive so as to resist bacterial growth prior to consumption of the food product.

It is yet another objective of this invention to provide a process of resisting the undesired growth of bacteria.

It is yet another objective of this invention to provide such an antibacterial product and method of use which will not have a detrimental effect on the desirable growth of *E. coli* bacteria.

These and other objects of the invention will be fully understood from the following description of the invention on reference to the illustrations appended hereto.

BRIEF DESCRIPTION OF THE DRAWINGS

FIGS. 1 through 4 are a series of plots of graded inhibition of bacterial growth due to increasing concentrations of polyunsaturated long-chain alcohol.

DESCRIPTION OF THE PREFERRED EMBODIMENTS

As used herein, in the absence of a clear, express indication to the contrary at a specific location, the term "orally administerable product" refers to a food or beverage product, a medicinal preparation including pharmaceuticals, a mouthwash and a cleansing agent such as toothpaste as well as other products which are adapted to be taken into the mouth of and/or swallowed by members of the animal kingdom including humans.

As used herein, in the absence of a clear, express indication to the contrary at a specific location, the term "locally administerable product" refers to a product adapted to be applied directly to an area to be treated either preventively or therapeutically and shall include but not be limited to antibacterial preparations, face and hand creams, cleansing creams, soaps, skin salves, lavage solutions and cosmetics.

As used herein, in the absence of an express indication to the contrary at a particular location, the term "patient" shall refer to members of the animal kingdom including humans regardless of whether they are at a particular time suffering from an ailment, being subjected to a diagnostic procedure or otherwise receiving medical treatment.

The present invention provides a method of inhibiting growth of certain bacteria by exposing the bacteria to an effective concentration of a polyunsaturated long-chain alcohol selected from the group consisting of linolenyl alcohol and linoleyl alcohol. More specifically, these alcohols have been found to be more effective in bactericidal effect than alcohols of corresponding chain length such as stearyl or oleyl in resisting growth of bacteria selected from the group consisting of *Clostridium butyricum, Clostridium perfringens, Streptococcus mutans, Streptococcus mutans BHT,* and *Streptococcus sanguis.*

As linolenyl alcohol and linoleyl alcohol are bactericidal at very low concentrations with respect to *Clostridium butyricum* and *Clostridium perfringens* which are known causes of food poisoning, low concentrations of these alcohols as food additives could serve to minimize food poisoning risks.

*Streptococcus mutans, Streptococcus mutans BHT* and *Streptococcus sanguis* are all believed to be involved in the development of dental caries and periodontal disease. Using linoleyl alcohol or linolenyl alcohol in mouthwash, toothpaste and oral treatment of the mouth could serve to resist formation of undesired dental caries and periodontal disease.

These alcohols could also be used in lavage solution to wash deep puncture wounds to prevent infections of *Clostridium perfringens.*

These alcohols could also be applied locally, as/or in a locally administerable product applied externally to treat or resist skin infection such as acne, for example. These may conveniently be applied as an antibacterial agent per se or incorporated in other products such as face creams, skin salves, soaps, cosmetics or other products.

Another advantage of these alcohols is that studies have shown that they are not bactericidal to *E. coli.* As the *E. coli* is a desirable form of bacteria in the gastrointenstinal tract, this is advantageous.

As linolenyl and linoleyl alcohols do not effect the growth of Hela cells in concentrations where the alcohols are effective as bactericidal agents they would be non-toxic if given to a patient.

In order to verify the effectiveness of these two alcohols as bactericidal agents, a series of tests were performed.

*Clostridium butyricum* (ATCC 6015) was maintained on fluid thioglycolate 1% agar stabs. Seed cultures were then prepared by innoculating the thioglycolate media with two loop fulls of *Clostridium butyricum* and placing the innoculum in an incubator at 37.5° C. overnight. At this time various concentrations and combinations of linoleyl, linolenyl and stearyl alcohol were introduced into 12 ml Klett tubes containing 7 ml of thioglycolate media. Ethanol was the vehicle in which the long-chain alcohols were dissolved. Stock solutions of the long-chain alcohols were dissolved in 95% ethanol and 40 μl (microliter) of this solution injected directly into the 7.0 ml incubation medium and the solution rapidly mixed on a "Vortex" for 30 seconds. The control cultures were treated in the same manner with the only addition being 40 μl of 95% ethanol. Duplicate tubes were prepared for each concentration. These pretreated tubes were placed in a gas Pak anaerobic jar (Bio-Quest Laboratories) and incubated overnight. At the end of this interval a 0.2 ml aliquot of *Clostridium butyricum*, which had been vigorously vortexed to distribute the bacteria, was transferred from the seed culture to each of the pre-treated Klett tubes. This innoculated media was incubated at 37.5° C. for two hours prior to mixing on a Vortex. The opacity of the mixed cultures was read with a Klett-Summerson Colorimeter (800-3) equipped with a #66 filter. Growth was measured by the change in opacity. This procedure was repeated every hour through eight hours. A final reading was then taken at 24 hours. The ultra-violet spectra of the stock solutions of linoleyl and linolenyl alcohol was recorded on a Perkin-Elmer spectrophotometer.

TABLE 1

| Experimental Condition | Incubation Interval Hours | | | | | | | | |
|---|---|---|---|---|---|---|---|---|---|
|  | 1 | 2 | 3 | 4 | 5 | 6 | 7 | 8 | 24 |
| Control N = 14 | 4 ± 1 | 10 ± 3 | 22 ± 6 | 42 ± 7 | 59 ± 7 | 76 ± 8 | 88 ± 10 | 102 ± 14 | 179 ± 9 |
| linoleyl (1.23) N = 8 | 5 ± 1 | 10 ± 4 | 19 ± 5 | 28 ± 5 | 39 ± 6 | 55 ± 7 | 62 ± 8 | 65 ± 4 | 156 ± 15 |
| linoleyl (1.84) N = 8 | 3 ± 0 | 8 ± 1 | 14 ± 2 | 23 ± 3 | 33 ± 4 | 42 ± 5 | 49 ± 6 | 54 ± 7 | 156 ± 15 |
| linolenyl (1.16) N = 5 | 2 ± 2 | 4 ± 3 | 7 ± 4 | 10 ± 7 | 16 ± 10 | 26 ± 17 | 23 ± 22 | 44 ± 33 | 140 ± 48 |
| linolenyl (1.74) N = 8 | | | | No Growth | | | | | 85 ± 63 |

The numbers in parentheses refer to the alcohol concentration in the final culture medium, expressed as nanomoles/ml. In each instance the values presented are the mean ±S.D. N=the number of independent observations.

Table 1 shows the results of the tests performed in exposing *Clostridium butyricum* to two different concentrations of linoleyl and linolenyl alcohol for time periods from one hour to 24 hours. Table 1 also shows the comparison of the results with a control group. The numbers in parentheses refer to the alcohol concentration in the final culture medium, expressed as nanomoles/ml. In each instance the values presented are the mean ±S.D. and N=the number of independent observations.

Table 1 shows the effect of trace amounts of linoleyl and linolenyl alcohol on the growth of *Clostridium butyricum.* The linoleyl alcohol was employed in concentrations of 1.23 nanomoles/ml and 1.84 nanomoles/ml. The linolenyl alcohol was employed in concentrations of 1.16 nanomoles/ml and 1.74 nanomoles/ml. Smaller concentrations of these alcohols were studied (0.62 nanomoles/ml of linoleyl and 0.57 nanomoles/ml of linolenyl alcohol), however the growth was not significantly different at these concentrations from that of the control cultures. Greater than 3 nanomoles/ml of either alcohol completely inhibited growth.

In reviewing the results, growth inhibition is defined as no change in opacity of the culture medium over a 24 hour incubation interval.

In comparing the two concentrations of linoleyl alcohol with that of the control cultures, statistically significant difference in growth (p less than 0.01) was noted after the fourth hour.

The average opacity of 28±5 observed in cultures treated with 1.23 nanomoles per ml linoleyl alcohol and 23±3 in cultures treated with 1.84 nanomoles linolenyl alcohol is 66% and 54% of the opacity, 42±7, observed in the control cultures.

With the exception of the second hour of growth, it is noted that in all instances the 1.84 nanomoles/ml of linoleyl alcohol produced a greater amount of growth inhibition with respect to the controlled culture than the lower concentration of linoleyl alcohol. After eight hours exposure to 1.23 and 1.84 nanomoles/ml of linoleyl alcohol resulted, respectively, in a 36% and a 46% inhibition in bacterial growth compared to the control.

With respect to the linolenyl alcohol concentrations of 1.16 nanomoles/ml and 1.74 nanomoles/ml a statistically significant difference in growth from that of the control (p less than 0.01) existed after the first hour. The inhibition of growth after eight hours for bacteria incubated with 1.16 nanomoles/ml of linolenyl alcohol was 57%, while with a concentration of 1.74 nanomoles/ml no growth was observed over the initial eight hour interval.

It would appear from these results that linolenyl alcohol is more effective in reducing growth of *Clostridium butyricum* than linoleyl alcohol. In comparing the lower concentrations of each of these two alcohols with the exception of the first hour of growth, exposure of the cells to 1.16 nanomoles/ml of linolenyl alcohol resulted in a significantly greater amount of growth inhibition than that observed on exposure of the same cells to 1.23 nanomoles/ml of linoleyl alcohol (p less than 0.01). The higher concentration of linolenyl alcohol (1.7 nanomoles/ml) was also more effective than the higher concentration of linoleyl (1.84 nanomoles/ml) in inhibiting growth over the 24 hour incubation period (p less than 0.01).

Table 2 illustrates the results of testing of the effects of exposing *Streptococcus mutans* to five different concentrations of linolenyl alcohol (3.2, 6.4, 9.6, 19.02 and 25.36 nanomoles/ml) for periods from one to 24 hours.

In performing the experimental work which generated the results reported in Table 2, seed cultures of *Streptococcus mutans* were grown overnight at 37° C. in Todd Hewitt Broth (Difco Laboratories). Bateria were suspended by Vortexing the overnight culture. Then 0.2 ml aliquots were removed from the cultures and added to 7.0 ml of fresh media. This media had been pretreated with 10 μl of L-ascorbic Acid (11.3μ moles) and the specified concentrations of linolenyl alcohol. The numbers in parentheses refer to the alcohol concentration in the final culture medium, expressed as nanomoles/ml. Growth was assessed by measuring the change in opacity observed with a Klett-Summerson colorimeter equipped with a #66 filter. In each instance the values presented are the mean ±S.D. N=the number of independent observations. Stock solutions of the long-chain alcohols were dissolved in 95% ethanol and 40 μl of this solution injected directly into the 7.0 ml incubation medium and the solution rapidly mixed on a "Vortex" for 30 seconds. The control cultures were treated in the same manner with the only addition being 40 μl of 95% ethanol.

TABLE 2

| Experimental Condition | Incubation Interval Hours 1 | 2 | 3 | 4 | 5 | 6 | 7 | 8 | 24 |
|---|---|---|---|---|---|---|---|---|---|
| Control N = 7 | 4 ± 2 | 19 ± 1 | 37 ± 1 | 60 ± 4 | 105 ± 11 | 130 ± 5 | 132 ± 6 | 133 ± 6 | 243 ± 4 |
| Linolenyl (3.2) N = 7 | 4 ± 2 | 13 ± 2 | 25 ± 4 | 43 ± 8 | 71 ± 19 | 116 ± 18 | 130 ± 3 | 130 ± 3 | 140 ± 7 |
| Linolenyl (6.4) N = 7 | No Growth | | | | 1 ± 1 | 2 ± 1 | 4 ± 1 | 8 ± 2 | 116 ± 10 |
| Linolenyl (9.6) N = 7 | No Growth | | | | | | | | 85 ± 20 |
| Linolenyl (19.02) N = 5 | No Growth | | | | | | | | 46 ± 27 |
| Linolenyl (25.36) N = 5 | No Growth | | | | | | | | 8 ± 6 |

It is noted that for concentrations of 6.4 nanomoles/ml and greater no growth occurred during the first four hours and for concentrations of 9.6 nanomoles/ml and greater no growth occurred during the first eight hours. Also, beginning with the second hour at all tested concentrations as compared with the control group there was significant inhibition of growth of the *Streptococcus mutans*.

FIG. 1 is a plot of the growth response in Klett units. A "Klett Unit" is a change in the opacity (change in transmitted light) of a solution when placed in a Klett Summerson colorimeter under specified conditions. It is a measure of cellular growth. The more cells the greater the opacity of a solution due to the greater amount of growth.

From this plot of *Streptococcus mutans* after 24 hours it is apparent that the degree of inhibition of bacterial growth observed is proportional to the log of the linolenyl alcohol concentration. In this instance a 50% inhibition in the growth response is observed at a linolenyl alcohol concentration of about 6.4 nanomoles per ml.

Table 3 illustrates the results of the effect of treatment of linolenyl alcohol on the growth of *Streptococcus mutans BHT.* Concentrations of linolenyl alcohol at five different levels (1.68, 2.54, 3.3, 6.4, 9.6 and 13.2 nanomoles/ml) were employed along with a control group. Seed cultures were grown in Todd Hewitt Broth employing growth conditions identical to those detailed in Table 2. The concentration of linolenyl alcohol (in parentheses) refers to the concentration in the final culture medium, expressed as nanomoles/ml.

TABLE 3

| Experimental Condition | Incubation Interval Hours | | | | | | |
|---|---|---|---|---|---|---|---|
| | 1 | 2 | 3 | 4 | 5 | 6 | 24 |
| Control N = 4 | 6 ± 2 | 15 ± 3 | 31 ± 5 | 54 ± 9 | 91 ± 17 | 132 ± 6 | 151 ± 6 |
| Linolenyl (1.68) N = 3 | 5 ± 0 | 13 ± 1 | 25 ± 1 | 46 ± 4 | 77 ± 10 | 122 ± 14 | 148 ± 2 |
| Linolenyl (2.54) N = 2 | 3 ± 1 | 8 ± 1 | 16 ± 2 | 28 ± 3 | 47 ± 35 | 78 ± 5 | 141 ± 1 |
| Linolenyl (3.3) N = 4 | 3 ± 1 | 6 ± 1 | 11 ± 2 | 21 ± 3 | 35 ± 4 | 64 ± 9 | 145 ± 6 |
| Linolenyl (6.4) N = 2 | | | No Growth | | | | 136 ± 3 |
| Linolenyl (9.6) N = 4 | | | No Growth | | | | 92 ± 31 |
| Linolenyl (13.2) N = 2 | | | No Growth | | | | 48 ± 24 |

It is noted that at concentrations of 6.4 nanomoles/ml and above no growth of the *Streptococcus mutans BHT* was experienced during the first six hours and that differences from the control group were noted even at the end of the first hour with concentrations as low as 1.68 nanomoles/ml.

Figure 1:
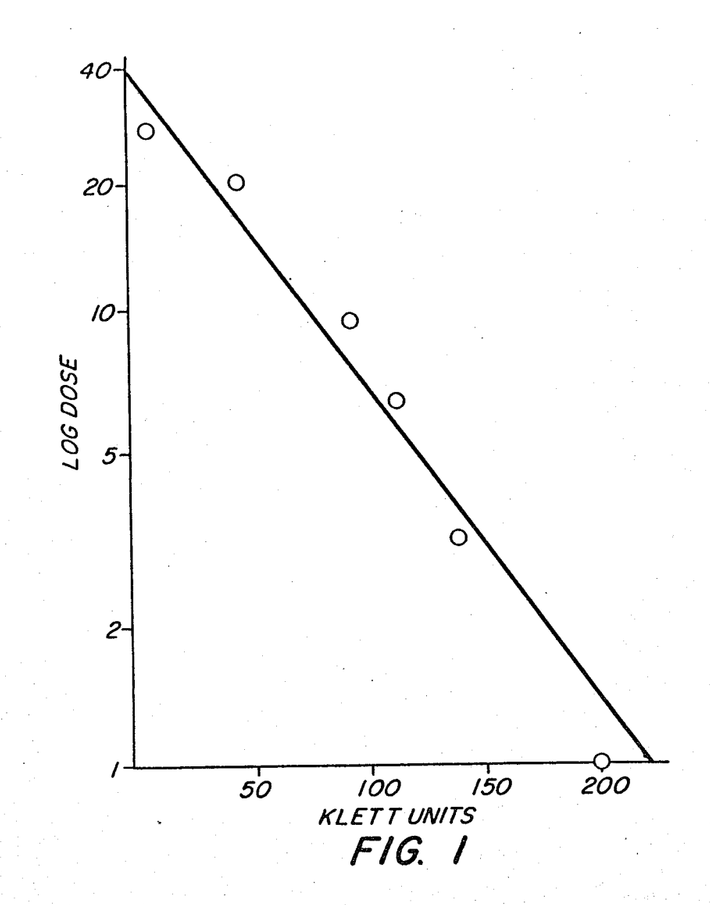
Figure 2:
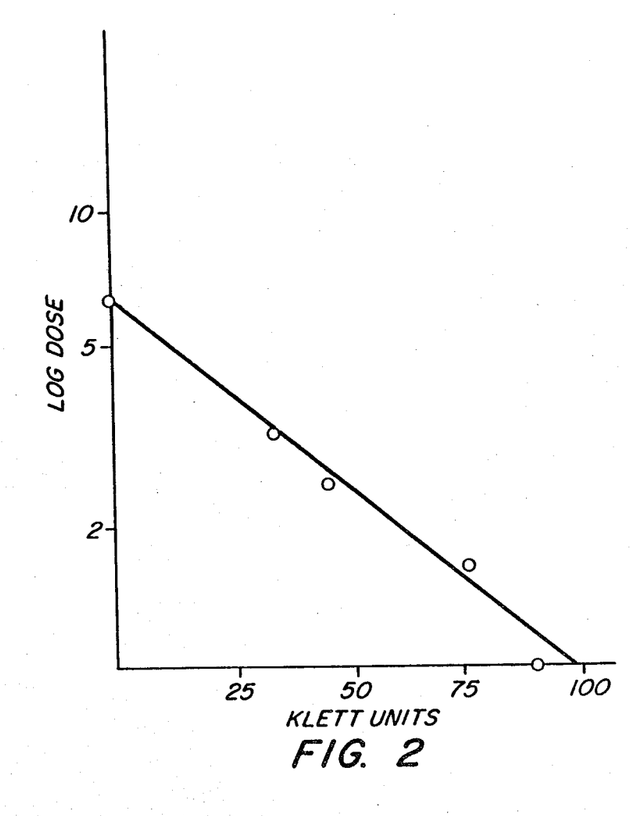

FIG. 2 is a plot of the growth response in Klett units of *Streptococcus mutans BHT* after five hours of incubation against the log of the several different concentrations of linolenyl alcohol.

Again the inhibition in the growth of bacterium is proportional to the log of the linolenyl alcohol concentration of the culture medium, a 50% inhibition in growth is achieved at an alcohol concentration of about 2.54 nanomoles per ml.

Table 4 illustrates tests of linolenyl alcohol on the growth of *Streptococcus sanguis*. Five different concentrations of linolenyl alcohol (1.68, 2.54, 3.2, 6.4 and 9.6 nanomoles/ml) were compared with the control group. Seed cultures, *Streptococcus sanguis* were grown in Todd Hewitt Broth employing growth conditions described to those detailed in Table 2.

the control group was noted at the second hour for a concentration of 2.54 nanomoles/ml and at the third hour for the 1.68 nanomoles/ml concentration.

Figure 3:
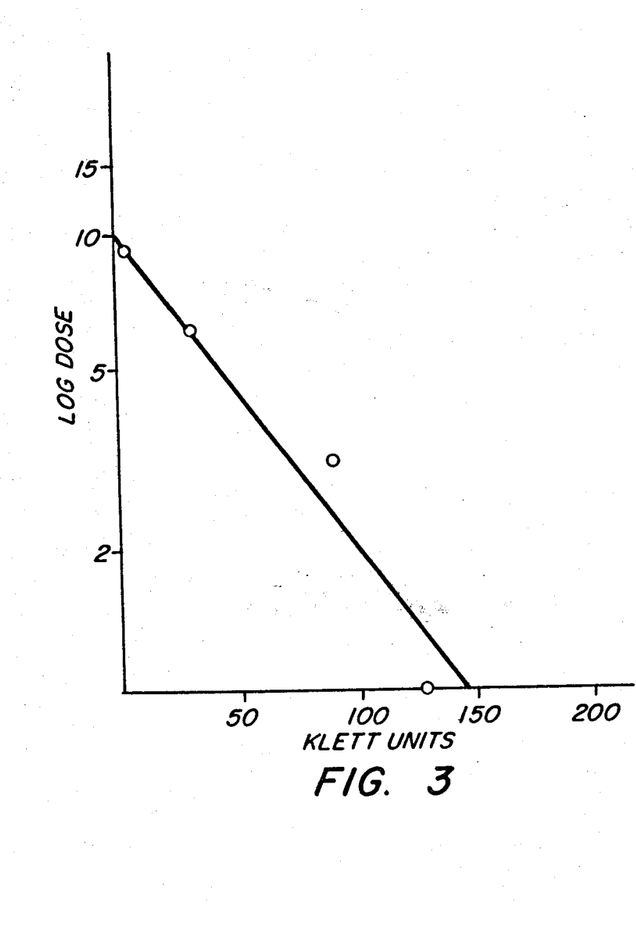
Figure 4:
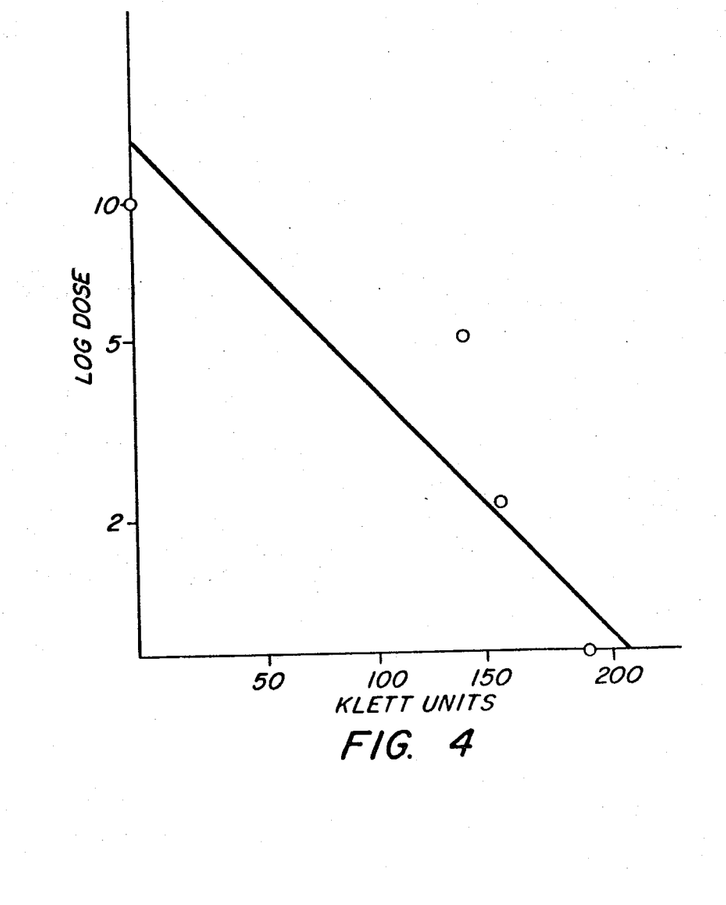

FIG. 3 illustrates the log dose response curve obtained by plotting the growth observed in Klett units of *Streptococcus sanguis* after a 24 hour incubation interval versus the log of the final linolenyl alcohol concentration in nanomoles/ml present in the culture medium.

From this plot it is readily apparent that a 50% inhibition in bacterial growth is observed at a linolenyl alcohol concentration of about 4.8 nanomoles per ml culture medium.

Table 5 illustrates the effect of linolenyl alcohol on the growth of *Streptococcus mutans, Streptococcus mutans BHT* and *Streptococcus sanguis*. Seed cultures were grown in Todd Hewitt Broth employing growth conditions identical to those detailed in Table 2. Sufficient linolenyl alcohol was added to the culture media to give a final concentration of 3.2 nanomoles/ml. The numbers above refer to the percent growth compared to each control of the individual oral bacteria i.e. 100 would be equal to 100% of the control. N=number of indepen-

TABLE 4

| Experimental Conditions | Incubation Interval Hours | | | | | | | | |
|---|---|---|---|---|---|---|---|---|---|
| | 1 | 2 | 3 | 4 | 5 | 6 | 7 | 8 | 24 |
| Control N = 3 | 1 ± 1 | 6 ± 1 | 18 ± 4 | 42 ± 8 | 89 ± 15 | 136 ± 3 | 136 ± 3 | 136 ± 3 | 126 ± 7 |
| Linolenyl (1.68) N = 2 | 1 ± 1 | 6 ± 1 | 13 ± 2 | 32 ± 3 | 56 ± 2 | 124 ± 13 | 128 ± 1 | 128 ± 1 | 227 ± 1 |
| Linolenyl (2.54) N = 2 | 1 ± 1 | 2 ± 1 | 3 ± 1 | 6 ± 0 | 8 ± 2 | 16 ± 4 | 32 ± 8 | 65 ± 8 | 121 ± 0 |
| Linolenyl (3.2) N = 2 | | | | No Growth | | | | | 93 ± 33 |
| Linolenyl (6.4) N = 2 | | | | No Growth | | | | | 36 ± 36 |
| Linolenyl (9.6) N = 2 | | | | No Growth | | | | | 7 ± 3 |

It is noted that for concentrations as low as 3.3 nanomoles/ml there was no growth of *Streptococcus sanguis* at the end of eight hours. Also, a departure from dent observations.

TABLE 5

| Experimental Condition | Incubation Interval Hours 1 | 2 | 3 | 4 | 5 | 6 | 24 |
|---|---|---|---|---|---|---|---|
| *Streptococcus mutans* N = 7 | 100 | 68 | 68 | 72 | 68 | 89 | 98 |
| *Streptococcus mutans* BHT N = 4 | 50 | 40 | 35 | 51 | 51 | 48 | 96 |
| *Streptococcus sanguis* N = 2 | 0 | 0 | 0 | 0 | 0 | 0 | 0 | linolenyl (3.3) IIA and 6.6 nanomoles/ml designated linolenyl (6.6) IIB was injected directly into tubes containing 7 ml of the growing innoculum. This same experimental procedure designated linolenyl (6.6) III was further implemented at the end of the sixth hour of growth in another group of cultures by adding sufficient linolenyl alcohol to achieve a final concentration of 6.6 nanomoles/ml. In this instance the values recorded are the mean ±S.D. of 5 separate experiments.

TABLE 6

| Experimental Condition | Incubation Interval Hours 1 | 2 | 3 | 4 | 5 | 6 | 7 | 8 | 9 | 10 | 11 | 12 | 24 |
|---|---|---|---|---|---|---|---|---|---|---|---|---|---|
| Control | 2±1 | 10±2 | 32±4 | 51±4 | 76±5 | 88±3 | 100±4 | 115±4 | 121±3 | 128±4 | 135±5 | 142±4 | 196±8 |
| Linolenyl-I (3.3) | | | | | | | No Growth | | | | | | |
| Linolenyl-IIA (3.3) | 3±1 | 13±4 | 32±8 | 30±7 | 5±3 | 1±1 | | | | No Growth | | | |
| Linolenyl-IIB (6.6) | 2±1 | 8±4 | 22±8 | 20±5 | | | | | No Growth | | | | |
| Linolenyl-III (6.6) | 1±1 | 9±1 | 31±4 | 50±5 | 74±6 | 84±3 | 93±4 | 54±3 | 49±3 | 47±2 | 45±3 | | 45±3 |

These results would indicate that "Streptococcus sanguis is the most sensitive of the Streptococci tested. Also, comparing the results with those of Table 1, it would appear that *Clostridium butyricum* is more sensitive to the toxic effect of the polyunsaturated alcohols than the Streptococci tested.

In order to obtain information regarding the effect of the addition of linolenyl alcohol to the culture medium in respect of inhibiting growth of established cultures of the *Clostridium butyricum,* additional testing was done. Seed cultures of *Clostridium butyricum* were grown overnight at 37° C. in fluid thioglycolate media employing growth conditions detailed in Table 1. In this instance the control culture was grown in media in which the only addition was 40 μl of 95% ethanol. In Table 6, linolenyl I represents a similar culture in which 40 μl of a solution of linolenyl alcohol in 95% ethanol was added at the start of the incubation interval. Linolenyl IIA and IIB are cultures where the 40 μl solution of linolenyl alcohol was added after an initial growth interval of three hours. Linolenyl III is the same culture system but the solution of linolenyl alcohol was not added until after an initial growth interval of six hours. The numbers in parentheses represent the concentration detailed in Table 1. At the end of the third hour of growth 40 μl of a solution containing 95% ethanol and a concentration of linolenyl alcohol that would result in a final concentration of 3.3 nanomoles/ml designated It is noted that with respect to linolenyl-I (3.3 nanomoles/ml) no growth of *Clostridium butyricum* occurred during the 24 hours. With respect to linolenyl-IIA growth was terminated at the seventh hour and with respect to linolenyl-IIB growth was inhibited at the fifth hour.

The results in this table indicate that at a concentration of 3.3 nanomoles per ml linolenyl alcohol completely inhibits the growth of *Clostridium butyricum* when initially present in the culture medium. The observation that adding sufficient linolenyl alcohol to a growing culture to yield a final concentration of 3.3 or 6.6 nanomoles per ml medium not only results in an inhibition of growth but a decrease in the opacity of the medium indicates that not only growth inhibition has occurred but that bacterial lysis and death has also occurred. Similar results are noted when the polyunsaturated alcohol is added to a culture that had been growing for a six hour interval, linolenyl-III. The effect of linolenyl alcohol in inhibiting growth of initial or established cultures of Clostridium perfringens is shown in Tables 7 and 8. Linolenyl alcohol was added to the cultures in a manner identical to that described in Table 1. The numbers in parentheses indicate the linolenyl alcohol concentration in nanomoles per ml media. Seed cultures of *Clostridium perfringens* were grown overnight at 37° C. on fluid thioglycolate media employing growth conditions identical to those detailed in Table 1. N=the number of independent observations. The concentration of linolenyl alcohol, nanomoles per ml, in the final culture media is represented by the numbers in parentheses.

TABLE 7

| Experimental Condition | Incubation Interval Hours 1 | 2 | 3 | 4 | 5 | 6 | 7 | 8 | 24 |
|---|---|---|---|---|---|---|---|---|---|
| Control N = 9 | 10 ± 1 | 34 ± 2 | 82 ± 6 | 122 ± 9 | 140 ± 13 | 151 ± 15 | 155 ± 16 | 161 ± 15 | 187 ± 22 |
| Linolenyl (2.1) N = 9 | — | 14 ± 1 | 30 ± 4 | 45 ± 6 | 61 ± 9 | 76 ± 5 | 89 ± 8 | 97 ± 7 | 157 ± 11 |
| Linolenyl (4.9) N = 4 | | | | | No Growth | | | | 140 ± 23 |
| Linolenyl (9.8) | | | | | No Growth | | | | |

TABLE 7-continued

| Experimental Condition | Incubation Interval Hours | | | | | | | | |
|---|---|---|---|---|---|---|---|---|---|
| | 1 | 2 | 3 | 4 | 5 | 6 | 7 | 8 | 24 |
| N = 4 | | | | | | | | | |

In the work reported in Table 8 seed cultures of *Clostridium perfringens* were grown overnight at 37° C. on fluid thioglycolate media employing growth conditions detailed in Table 1. At the end of the third hour of growth 40 μl of a solution containing 95% ethanol and sufficient linolenyl alcohol to yield a final concentration of 19.7 nanomoles/ml in the culture medium was injected directly into tubes containing 7 ml of the growing innoculum. The concentration of the alcohol (in parentheses) is expressed as nanomoles/ml incubation media. N=number of independent observations.

TABLE 8

| Experimental Condition | Incubation Interval Hours 1 | 2 | 3 | 4 | 5 | 6 | 7 | 8 | 24 |
|---|---|---|---|---|---|---|---|---|---|
| Control N = 9 | 10 ± 1 | 34 ± 2 | 82 ± 6 | 122 ± 9 | 140 ± 12 | 151 ± 15 | 155 ± 16 | 161 ± 15 | 187 ± 22 |
| Linolenyl (19.7) N = 2 | 12 ± 1 | 39 ± 1 | 91 ± 1 | 86 ± 1 | 79 ± 1 | 70 ± 1 | 70 ± 2 | 70 ± 1 | 66 ± 2 |

From the results presented in Table 7, it is apparent that when included in the culture medium at low concentrations, 2.1 nanomoles per ml, linolenyl alcohol causes a 40% inhibition of bacterial growth as compared to the control culture over an initial eight hour incubation interval. As the concentration of linolenyl alcohol in the culture medium is increased a more pronounced inhibition in growth is observed, no growth occurring at a linolenyl alcohol concentration of 9.8 nanomoles per ml.

The effect of adding linolenyl alcohol to a growing culture of *Clostridium perfringens* is depicted in Table 8. In this instance not only is growth inhibition achieved, but the observed decrease in opacity of the media indicates that cell death and lysis has also occurred. From these results it appears that at adequate concentrations linolenyl alcohol is not only bacteriostatic, but also bactericidal for *Clostridium perfringens.*

FIG. 4 is the plot of the growth response in Klett units of *Clostridium perfringens* after 24 hour incubation as against the log of the final linolenyl alcohol concentration in nanomoles/ml present in the culture medium.

In order to verify the fact that in inhibiting growth of the bacteria desired to be restricted, the linoleyl alcohol did not have a detrimental effect on the growth of desirable *Escherichia Coli* (*E. coli*) the effects of linoleyl on the growth of *Escherichia Coli* K-40 were tested with the results shown in Table 9. Seed cultures were grown in Todd Hewitt Broth employing growth conditions identical to those detailed in Table 2. N=number of independent cultures. The number in parentheses is the final concentration of linolenyl alcohol in the culture medium in nanomoles per ml.

TABLE 9

| Experimental Condition | Incubation Interval Hours 1 | 2 | 3 | 4 | 5 | 6 | 7 | 8 |
|---|---|---|---|---|---|---|---|---|
| Control N = 10 | 4 ± 1 | 18 ± 1 | 51 ± 5 | 78 ± 1 | 86 ± 2 | 87 ± 2 | 90 ± 2 | 89 ± 2 |
| Linolenyl (3.17) N = 11 | 3 ± 1 | 14 ± 5 | 44 ± 3 | 72 ± 2 | 84 ± 2 | 86 ± 2 | 87 ± 2 | 88 ± 2 |
| Linolenyl (6.3) N = 11 | 1 ± 0 | 2 ± 1 | 8 ± 3 | 23 ± 11 | 54 ± 11 | 77 ± 3 | 83 ± 1 | 86 ± 3 |

As the data clearly shows, there is no appreciable negative effect of linolenyl alcohol in concentrations of 3.17 nanomoles/ml and 6.3 nanomoles/ml on the growth of *E. coli.*

In order to compare the effects of linolenyl alcohol on *Clostridium butyricum* with other alcohols, comparative tests were performed employing linolenyl alcohol and stearyl alcohol, an 18 carbon saturated primary alcohol. Linolenyl alcohol is an 18 carbon polyunsaturated alcohol. Seed cultures were grown in fluid thioglycolate media employing growth conditions identical to those detailed in Table 1. The concentrations of the alcohols bracketed by parentheses are expressed as nanomoles/ml inducation media. N=number of independent observations.

TABLE 10

| Experimental Condition | Comparison of the Effects of Linolenyl Alcohol and Stearyl Alcohol on the Growth of *Clostridium butyricum* Hours 1 | 2 | 3 | 4 | 5 | 6 | 7 | 8 | 24 |
|---|---|---|---|---|---|---|---|---|---|
| Control N = 14 | 4 ± 1 | 10 ± 3 | 33 ± 6 | 42 ± 7 | 59 ± 7 | 76 ± 8 | 88 ± 10 | 102 ± 14 | 179 ± 9 |

TABLE 10-continued Comparison of the Effects of Linolenyl Alcohol and Stearyl Alcohol on the Growth of *Clostridium butyricum*

| Experimental Condition | Hours | | | | | | | | |
|---|---|---|---|---|---|---|---|---|---|
| | 1 | 2 | 3 | 4 | 5 | 6 | 7 | 8 | 24 |
| Stearyl (21.5) N = 14 | 5 ± 1 | 12 ± 3 | 25 ± 6 | 44 ± 9 | 61 ± 9 | 75 ± 9 | 88 ± 11 | 102 ± 14 | 181 ± 5 |
| Linolenyl (1.16) N = 5 | 2 ± 2 | 4 ± 3 | 7 ± 4 | 10 ± 7 | 16 ± 10 | 26 ± 17 | 33 ± 22 | 44 ± 33 | 140 ± 48 |
| Linolenyl (1.16) + Stearyl (21.5) N = 5 | 3 ± 1 | 7 ± 1 | 13 ± 2 | 22 ± 5 | 31 ± 9 | 43 ± 12 | 52 ± 16 | 72 ± 22 | 158 ± 17 |
| Linolenyl (1.74) N = 8 | | | | | No Growth | | | | 85 ± 16 |
| Linolenyl (1.74) + Stearyl (21.5) N = 5 | 1 ± 1 | 4 ± 2 | 7 ± 4 | 13 ± 8 | 20 ± 13 | 28 ± 19 | 37 ± 24 | 49 ± 33 | 140 ± 35 |

As is clearly shown in Table 10 linolenyl alcohol in a concentration of 1.16 nanomoles/ml performs substantially better than stearyl alcohol in a concentration of 21.5 nanomoles/ml. In fact, the performance of the stearyl alcohol is essentially identical with the control. Combinations of linolenyl with stearyl alcohol produced inferior results in the corresponding performance of linolenyl employed alone.

While for purposes of convenience, certain materials were described herein as suitable vehicles for use of the alcohols, it will be appreciated that a wide range of non toxic organic substances, such as propylene glycol, for example, may advantageously be employed.

While for many purposes, the method and product of this invention will be administered orally or locally to a patient, other uses such as applications to buildings, vehicles and other local application may be advantageous, and fall within the scope of this invention.

It will, therefore, be appreciated that the present invention has provided effective control of bacteria including anaerobic bacteria selected from the group consisting of *Clostridium butyricum, Clostridium perfringens, Streptococcus mutans, Streptococcus mutans BHT* and *Streptococcus sanguis*, by employing polyunsaturated long-chain alcohol selected from the group consisting of linoleyl alcohol and linolenyl alcohol. All of this is accomplished in an unforeseen fashion and provides means for employing the same orally administerable products and locally administerable products as well as other products.

Whereas particular embodiments of the invention have been described above for purposes of illustration it would be evident to those skilled in the art that numerous variations of the details may be made without departing from the invention as defined in the appended claims.

I claim:

1. A method of inhibiting growth of bacteria comprising
   exposing said bacteria to an effective concentration of polyunsaturated long-chain alcohol selected from the group consisting of linolenyl alcohol and linoleyl alcohol,
   providing said alcohol is an orally or locally administerable product, and
   providing said alcohol in toothpaste.

2. A method of inhibiting growth of bacteria comprising
   exposing said bacteria to an effective concentration of a polyunsaturated long-chain alcohol selected from the group consisting of linolenyl alcohol and linoleyl alcohol,
   providing said alcohol is an orally or locally administerable product, and
   providing said alcohol in mouthwash.

3. A bactericidal product comprising an orally or locally administerable product,
   an effective concentration of an antibacterial compound selected from the group consisting of linolenyl alcohol and linoleyl alcohol provided in said administerable product whereby said administerable product will resist growth of bacteria selected from the group consisting of *Clostridium butyricum, Clostridium perfringens, Streptococcus mutans, Streptococcus mutans BHT* and *Streptococcus sanguis*, and
   said orally administerable product is a toothpaste.

4. A bactericidal product comprising
   an orally or locally administerable product,
   an effective concentration of an antibacterial compound selected from the group consisting of linolenyl alcohol and linoleyl alcohol provided in said administerable product whereby said administerable product will resist growth of bacteria selected from the group consisting of *Clostridium butyricum, Clostridium perfringens, Streptococcus mutans, Streptococcus mutans BHT* and *Streptococcus sanguis*, and
   said orally administerable product in a mouthwash.

* * * * *

UNITED STATES PATENT AND TRADEMARK OFFICE
CERTIFICATE OF CORRECTION

PATENT NO. : 4,340,628

DATED : July 20, 1982

INVENTOR(S) : JOHN R. GILBERTSON and RICHARD J. CROUT

It is certified that error appears in the above-identified patent and that said Letters Patent are hereby corrected as shown below:

In Table 2, under the "24" column, the fourth equation down which reads "85 ± 20" should read --95 ± 20--.

Column 5, line 50, "1.7" should be --1.74--.

Column 5, line 62, "Bateria" should read --Bacteria--.

Column 9, line 30, the quotation marks should be deleted.

Claim 4, last line, "in a mouthwash" should read --is a mouthwash--.

Signed and Sealed this

*Fifth* Day of *October 1982*

[SEAL]

*Attest:*

*Attesting Officer*

GERALD J. MOSSINGHOFF

*Commissioner of Patents and Trademarks*